(12) United States Patent
Selner

(10) Patent No.: US 8,139,822 B2
(45) Date of Patent: Mar. 20, 2012

(54) DESIGNATION OF A CHARACTERISTIC OF A PHYSICAL CAPABILITY BY MOTION ANALYSIS, SYSTEMS AND METHODS

(76) Inventor: Allen Joseph Selner, Manhattan Beach, CA (US)

( * ) Notice: Subject to any disclaimer, the term of this patent is extended or adjusted under 35 U.S.C. 154(b) by 184 days.

(21) Appl. No.: 12/792,088

(22) Filed: Jun. 2, 2010

(65) Prior Publication Data

US 2011/0052005 A1    Mar. 3, 2011

Related U.S. Application Data

(60) Provisional application No. 61/238,039, filed on Aug. 28, 2009, provisional application No. 61/328,614, filed on Apr. 27, 2010.

(51) Int. Cl.
*G06K 9/00* (2006.01)
(52) U.S. Cl. ............................ 382/107; 73/491; 348/154
(58) Field of Classification Search .................. 382/100, 382/103, 106, 107, 128, 130; 73/488–494; 348/154, 155; 356/27–28.5
See application file for complete search history.

(56) References Cited

U.S. PATENT DOCUMENTS

| | | | |
|---|---|---|---|
| 4,891,748 A | 1/1990 | Mann | |
| 5,413,116 A | 5/1995 | Radke et al. | |
| 5,524,645 A | 6/1996 | Wills | |
| 5,662,118 A | 9/1997 | Skubick | |
| 5,687,716 A | 11/1997 | Kaufmann et al. | |
| 5,694,340 A | 12/1997 | Kim | |
| 5,810,747 A | 9/1998 | Brudny et al. | |
| 5,891,060 A | 4/1999 | McGregor | |
| 6,056,671 A | 5/2000 | Marmer | |
| 6,152,890 A | 11/2000 | Kupfer et al. | |
| 6,248,063 B1 | 6/2001 | Barnhill et al. | |
| 6,275,806 B1 | 8/2001 | Pertrushin | |
| 6,371,123 B1 | 4/2002 | Stark | |
| 6,514,219 B1 * | 2/2003 | Guimond et al. | 600/595 |
| 6,561,992 B1 | 5/2003 | Eberhart et al. | |
| 6,944,317 B2 | 9/2005 | Pavlovic et al. | |
| 6,945,911 B2 | 9/2005 | Jackowski | |
| 6,974,326 B2 | 12/2005 | Marple-Horvat | |

(Continued)

FOREIGN PATENT DOCUMENTS

GB    2447915 A    10/2008

(Continued)

OTHER PUBLICATIONS

Bartlett, Roger, Artificial Intelligence in Sports Biomechanics: New Dawn or False Hope?, The 8th Australasian Conference on Mathematics and Computers in Sport, Jul. 3-5, 2006, Queensland, Australia. Published (online): Dec. 15, 2006.

(Continued)

*Primary Examiner* — Anand Bhatnagar
(74) *Attorney, Agent, or Firm* — George P. White

(57) ABSTRACT

Motion Analysis is used to classify or rate human capability in a physical domain via a minimized movement and data collection protocol producing a discreet, overall figure of merit of the selected physical capability. The minimal protocol is determined by data mining of a more extensive movement and data collection. Protocols are relevant in medical, sports and occupational applications. Kinematic, kinetic, body type, Electromyography (EMG), Ground Reactive Force (GRF), demographic, and psychological data are encompassed. Resulting protocols are capable of transforming raw data representing specific human motions into an objective rating of a skill or capability related to those motions.

39 Claims, 7 Drawing Sheets

U.S. PATENT DOCUMENTS

| | | | |
|---|---|---|---|
| 7,074,168 | B1 | 7/2006 | Farnes et al. |
| 7,096,206 | B2 | 8/2006 | Hitt |
| 7,181,375 | B2 | 2/2007 | Rao et al. |
| 7,264,554 | B2 * | 9/2007 | Bentley .................. 473/222 |
| 7,343,197 | B2 | 3/2008 | Shusterman |
| 7,502,498 | B2 * | 3/2009 | Wen et al. .............. 382/128 |
| 7,702,140 | B2 * | 4/2010 | Hirsch et al. ........... 382/128 |
| 7,769,207 | B2 * | 8/2010 | Olivo et al. ............. 382/115 |
| 7,882,135 | B2 * | 2/2011 | Brunner et al. ......... 707/791 |
| 7,931,604 | B2 * | 4/2011 | Even Zohar et al. .... 600/595 |
| 2001/0034730 | A1 | 10/2001 | Bhandari et al. |
| 2003/0166996 | A1 | 9/2003 | Kim et al. |
| 2004/0220490 | A1 | 11/2004 | Appel |
| 2005/0234309 | A1 | 10/2005 | Klapper |
| 2005/0240086 | A1 | 10/2005 | Akay |
| 2006/0084850 | A1 | 4/2006 | Spinner et al. |
| 2008/0269644 | A1 | 10/2008 | Ray |

FOREIGN PATENT DOCUMENTS

| | | |
|---|---|---|
| WO | WO2004049944 A1 | 6/2004 |
| WO | 2007-029012 | 3/2007 |
| WO | WO2007029012 A1 | 3/2007 |
| WO | WO2007062519 A1 | 6/2007 |

OTHER PUBLICATIONS

Barker AL, Nitz JC, Low Choy NL, Haines TP, Clinimetric Evaluation of the Physical Mobility Scale Supports Clinicians and Researchers in Residential Aged Care. Arch Phys Med Rehabil vol. 89, 2140-5, Nov. 2008.

Keenan A-M, Redmond AC, Horton M. Conaghan PG, Tennant A. The Foot Posture Index: Rasch Analysis of a Novel, Foot-Specific Outcome Measure. Arch Phys Med Rehabil vol. 88, 88-93 Jan. 2007.

Lafuente R, Belda JM, Sanchez-Lacuesta J, Soler C, Prat J, Design and test of neural networks and statistical classifiers in computer-aided movement analysis: a case study on gait analysis. Clinical Biomechanics, vol. 13, No. 3, pp. 216-229, 1997, 1998 Elsevier Science Ltd. Printed in Great Britian.

Eskofier, Bjoern and Hoenig, Florian, Kuehner, Pascal. Classification of Perceived Running Fatigue in Digital Sports. IEEE Xplore digital library, Jan. 23, 2009, from 19th International Conference on Pattern Recognition, 2008 ICPR Dec. 8-11, 2008 pp. 1-4 Tampa, FL.

Schollhorn, W.I., Applications of artifical neural nets in clinical biomechanics, Elsevier Ltd, Clinical Biomechanics 19 (2004) 876-898.

Lau, Hong-Yin, Tong, Kai-Yu, Zhu, Hailong. Support vector machine for classification of walking conditions of persons after stroke with dropped foot. 2009 Elsevier B.V., Human Movement Science 28 504-514.

Armand, Stephane, Watelain, Eric, Roux, Emmanuel, Mercier, Moise and Lepoutre, Francois-Xavier. Linking clinical measurements and kinematic gait patterns of toe walking using fuzzy decision trees. 2007 Elsevier B.V., Gait & Posture 25 475-484.

Kim JY, Parnianpour M, Marras WS, Quantitative assessment of the control capability of the trunk muscles during oscillatory bending motion under a new experimental protocol. 1996 Elsevier Science Limited. Clinical Biomechanics, vol. 11, No. 7 385-391 in Great Britain.

Daffertshofer A, Lamoth CLC, Meijer OG, Beek PJ, PCA in studying coordination and variability: a tutorial. Elsevier Clinical Biomechanics 2004, 19 415-428.

Begg R, Kamruzzaman J, A machine learning approach for automated recognition of movement patterns using basic, kinetic and kinematic gait data. Elsevier Journal of Biomechanics 2005, 38 401-408.

Bonato P, Mork PJ, Sherrill DM, Westgaard RH, Data Mining of Motor Patterns Recorded with Wearable Technology. IEEE Enigineering in Medicine and Biology Magazine, May/Jun. 2003.

Armand S, Watelain E, Mercier M, Lensel G, Lepoutre F-X, Identification and classification of toe-walkers based on ankle kinematics, using a data-mining method. Elsevier Gait & Posture 2006 23 240-248.

Vannozzi G, Cereatti A, Mazza C, Benvenuti E, Della Croce U, Extraction of information on elder motor ability from clinical and biomechanical data through data mining. Elsevier Computer Methods and Programs in Biomedicine 2007 88 85-94.

Greer S, Chambliss L, Mackler L, What physical exam techniques are useful to detect malingering? Journal of Family Practice, Aug. 2005.

Wolf S, Loose T, Schablowski M, Doderlein L, Rupp R, Gerner H, Bretthauer G, Mikut R, Automated feature assessment in instrumented gait analysis. Elsevier Gait & Posture 2006 23 331-338.

Tingley M, Wilson C, Biden E. Knight WR, An index to quantify normality of gait in young children. Elsevier Gait & Posture 2002 16 149-158.

Schwartz MH, Rozumalski A, The gait deviation index: A new comprehensive index of gait pathology. Elsevier Gait & Posture 2008 28 351-357.

Dona G, Principal Component Analysis for Motor Skills Characterization and Individual Monitoring in Sports Science. University DiPadova Thesis Jan. 2008, Italy.

Carriero A, Zavatsky A, Stebbins J, Theologis T, Shefelbine SJ. Determination of gait patterns in children with spastic diplegic cerebral palsy using principal components. Elsevier Gait & Posture 2009 29 71-75.

Lee JY, Hoff W, Activity Identification Utilizing Data Mining Techniques. Proceedings of he IEEE Workshop on Motion and Video Computing 2007, Austin, TX USA.

Lakany, Heba Extracting a diagnostic gait signature. Elsevier 2008 Pattern Recognition 41 1627-1637.

* cited by examiner

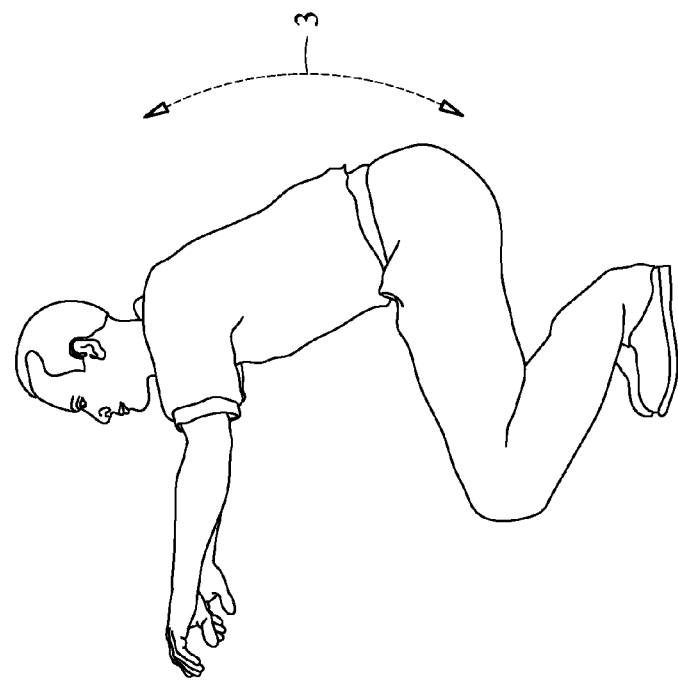
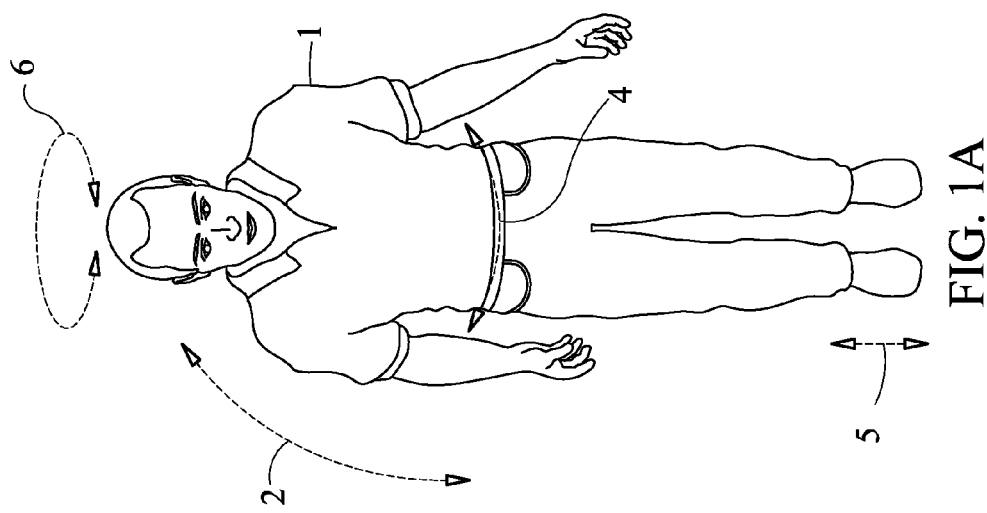
FIG. 1B
FIG. 1A

DESIGNATION OF A CHARACTERISTIC OF A PHYSICAL CAPABILITY BY MOTION ANALYSIS, SYSTEMS AND METHODS

RELATED APPLICATIONS

This application claims priority from U.S. provisional application 61/238,039 filed Aug. 28, 2009, and from U.S. provisional application 61/328,614 filed Apr. 27, 2010 which are hereby incorporated herein by reference in their entirety.

FIELD

Embodiments of this invention include the analysis of human movements to assign a classification or rating to a physical capability or condition related to those movements.

BACKGROUND

Kinematic and kinetic measurements have been made for the purpose of understanding human physiology, for diagnosing disorders, for sports study, and for sport performance improvement. Movement data has been collected by a variety of measurement techniques including by devices attached to the body, and by cameras detecting movement of body parts, and by detecting movement of specially marked points on a body.

Specialized sports, clinical, and research use of this technology have included the coaching of elite athletes, predicting the later appearance of Cerebral Palsy symptoms in infants, and tracking improvements over a course of treatment. Costs of dynamic body motion and force measurement devices have lowered and biomechanical knowledge has increased. However, the wide array and complexity of possible human motions, the large amount of raw data generated, and particularly a lack of results that are useful without expert interpretation, have significantly limited the routine exploitation of the tools and techniques of this field. Inexpensive and routinized solutions to incorporate motion-based measurements into everyday health care can have a great importance in overall cost control.

SUMMARY

There are sources of movement data collection that can provide volumes of information from instrumented movements. The teachings herein can make biomechanical data relevant to clinicians and coaches by producing and using protocols that can provide understandable ratings relevant to a physical task of interest. Motion test protocols can advantageously be administrable by modestly trained individuals and provide results rapidly and preferably relatively automatically.

Methods and systems taught herein can include an ordinal or scalar rating or an objectively defined discreet classification. These ratings and classifications can be of a physical capability or physical performance based on measurements made during performance of prescribed movement protocol. A set of predetermined, relevant movement-related information can be collected for analysis. The collected information can be analyzed in light of predetermined criteria to produce an objective classification or rating. Various applications of these teachings can have distinct executable movement and measurement protocols. Data mining techniques can be used over data representation of a large group of individuals to identify key parameters of movements to allow unknown subject's to be classified. Methods and systems for performing tests and producing a quantified rating of subjects, as well as methods and systems for creating such protocols, are within the teaching herein.

BRIEF DESCRIPTION OF DRAWINGS

The various drawings are to better illustrate the concepts described herein and to better teach those skilled in the art to make, use, and carry out these teachings. They are not intended to be limiting or to set metes and bounds.

FIG. 1A shows a human in a schematic view and indicates examples of some motions that might be included in developing a protocol;

FIG. 1B shows a human in a schematic view and a further example of a motion that might be included in developing a protocol;

DETAILED DESCRIPTION

Introduction

Figure 2A:
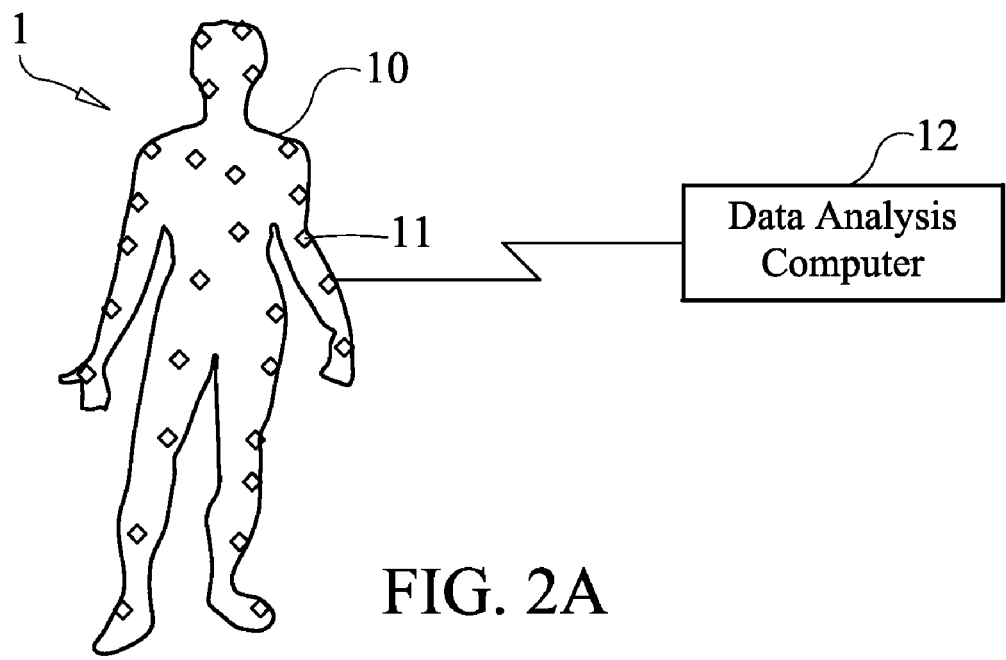
FIG. 2A illustrates one possibility for instrumentation of a human's motion involving a body suit with embedded motion and direction sensors.

Methods and Systems for developing and using evaluative test protocols are described by way of example embodiments. By protocol, as used herein, generally mean (a) a preplanned set of steps or actions to gather particular information related to a subject, student or patient; (b) a preplanned series of steps and actions to analyze, scale, compare, or transform that "raw" information and; (c) a predetermined method and criteria for assigning a rating, score, index or labeled classification based upon the information analysis. While a full protocol would include the steps of (a), (b), and (c) above, the term protocol can signify these steps individually. A trivial example of a protocol would be the steps for taking someone's blood pressure. A more complex protocol might be the series of steps involved in preparing a patient, configuring equipment, and administering an MRI scan.

Data mining includes mathematical and computational techniques of unstructured analysis and correlation between multiple parameters. These techniques help to uncover unexpected relationships between the parameters. When the data forms in relatively tight groupings those groupings can be called clusters.

The examples presented include both methods for developing a specific protocol and the performance of those executable protocols to transform motion data representative of an individual's performance into a readily understood classification or figure of merit.

EXAMPLES

The many areas of relevant human physical capability assessment include, for example: sports training, occupational choices, geriatric assessments, medical treatment progression, medical diagnostics, and malingering detection. Other areas of human physical activity relevant to the teachings herein include physical therapy, exercise routines, and game playing. Despite the availability of low-cost motion and force sensors and a rich understanding of biomechanics, assessments are nonetheless routinely made in a subjective manner or by static measurements such as range-of-motion. Alternatively, there are motion labs that can produce volumes of real-time raw motion information from which it may be difficult to draw conclusions. Some automatic and semi-automatic methods and systems applying these teachings have the potential to significantly lower a wide set of health care costs by adding quantized motion-related measurements to everyday medical care.

Examples of the teachings herein can use data mining techniques to semi-automatically analyze a set of collected movement and non-movement related parameters. That analysis can determine the statistical significance of each member of the set of parameters, in regards to a correlated attribute. A subset of more significant tests from the original comprehensive set of information can be identified for incorporation into an efficient executable protocol on a Pareto principle basis.

Method Overview

Embodiments of protocols for objective, repeatable, and quantified ratings based on kinematic, kinetic and other data can be developed by:

(1) Applying subject domain knowledge to postulate a comprehensive universe of movements and a comprehensive universe of collectable data to be representative of parameters of those movements. (2) For a set of subjects with known attributes in the particular domain of interest: directing subjects to perform the predetermined universe of movements while instrumented to collect data regarding the universe of parameters.

(3) Analyzing the collected data with linear and non-linear mathematical and computational methods. Those methods can include: multivariate regression, neural networks, and data mining by classification, clustering, self-organizing maps, and other approaches. The goal of the analysis can be to find parameters that correlate with the subjects' pre-known capabilities.

(4) Organizing the parameters by their predictive power or correlative strength.

(5) Building up a list of movements and their respective parameters to produce an executable protocol from a subset of the original universe of movements. The subset collectively having a desired level of overall predictive and correlative power.

Protocols consistent with the principles herein can also involve measuring non-motion parameters such as EMG (Electromyogram) and Ground Reactive Force (GRF) information and can also involve static variables such as body type, demographic, physiological, static biomechanical factors, and psychological information.

Example 1

Back Pain Assessment

In the case of back pain assessment, a set of subjects with known, varying degrees of impairment are tested.

With some clinical insight, a comprehensive set of motions are prescribed for subjects to perform while a comprehensive set of parameters characterizing those movements is collected. FIGS. 1A and 1B illustrate a person 1 and a variety of possible prescribed motions. For example, subjects may be instructed to bend in one or more specific directions 2, to stand from a sitting position 3, to twist body portions 4 at various rates, to walk normally, and turn or move various body parts 5 6. Motions might be repeated multiple times. Prescribed motions might comprise motions that are performed under load and those that are not loaded or with a different degree of load. Both motions that involve biomechanically open kinetic chains and those that involve closed kinetic chains might be used.

Figure 2B:
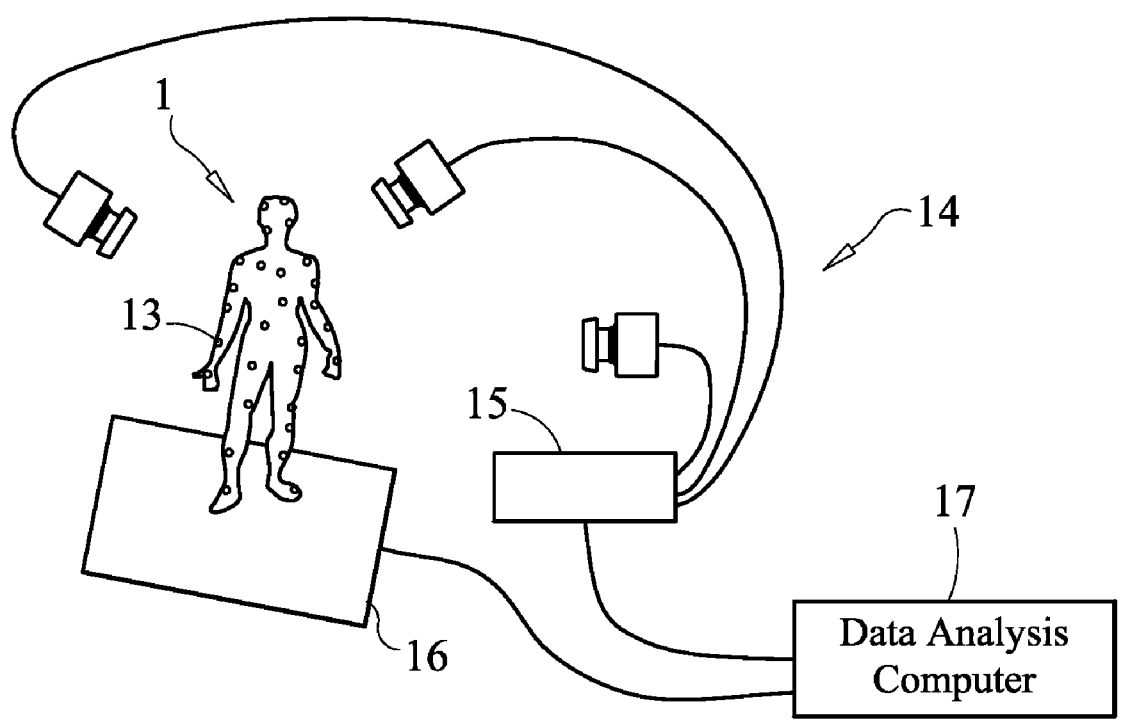
FIG. 2B illustrates one possibility for instrumentation of a human's motion using visual markers in various body locations viewed by multiple cameras for 3D position determination.

Those skilled in the art will recognize that there are many ways to collect human movement related parameters. FIGS. 2A and 2B illustrate alternate methods of 3D real-time full-body instrumentation. FIG. 2A schematically represents a person wearing a full body suit 10 and points out locations of embedded motion and direction sensors 11 that communicate with a data analysis computer 12. FIG. 2B, in contrast, shows a person with a plurality of marked spots 13. A multi-camera system 14 provides an apparatus to track the location of each spot in real time via a 3D tracking system 15. Some versions use passive spots and others can use actively light emitting spots. The tracked spot data and data from a pressure plate 16 are analyzed by a data analysis computer 17. In addition to positions in space, other parameters such as changes in joint angles and EMG data could be determined as well.

Each of the subjects with known capabilities or known impairments performs the determined set of motions while instrumented. The information is accepted and stored. The large volume of information resulting from the above tests is analyzed with non-linear techniques including artificial neural nets (ANN), self-organizing maps (SOM), machine learning classification trees, fuzzy classification, and other data mining techniques. Analysis by regression, multivariate analysis, and other more traditional statistical methods may be employed.

These analyses can produce a clustering of the various subjects' performance into discreet classifications or can find correlative statistical significance between the parameters and the known categorization of capabilities of the various subjects. An additional step is to then produce a subset of the initial motions and initial parameters that are particularly sensitive and have statistically significant power in indicating a classification membership or a rating. As those familiar with the art will understand, this is accomplished by further statistical analysis to identify the motions and the parameters associated with those motions that have the greatest predictive power in associating an individual with a cluster, a classification, or a rating. Starting from the most sensitive motion and related parameters on down, a list of motions and measurements is compiled for potential addition to an executable protocol until a desired balance between ease of protocol administration and statistical reliability is achieved. That list of motions and their associated salient parameters become the basis for an executable protocol. Rather than strictly using the top ranked motions and parameters as the basis of an executable protocol, tradeoffs between predictive power and ease of performing the various movements and measuring the various parameters may be made as well. A protocol can be devised that makes trade-offs between time to administer, cost, and complexity of instrumentation, versus confidence in a test's conclusions.

In the case of back pain the subjects have a range of back pain of known severity including some with no back pain. That information is compared to the collected movement parameters. The resulting protocol is intended to produce an overall measure of back impairment or back health that might be used to objectively assess progress over a course of therapy. For back pain assessment or for general back performance capability, a scalar index of 1-10 can apply.

Example 2

Malingering Assessment

A second application example, also related to back pain, is a protocol for detection of malingering or "sincerity of effort". Rather than result in a scalar index of back health this protocol produces a two-state classification of insincere/sincere effort or faking/not-faking within stated confidence levels. Following the teaching herein, a range of possible movements and measures of those movements were postulated and information regarding those particular factors was measured and analyzed for both actual back pain sufferers and for control subjects. One hypothesis of this assessment was that chronic back pain would result in a fairly consistent motion characteristic as the "point of pain" was entered in performing a prescribed movement. In other words, if a subject was asked to perform a task that resulted in back pain, he or she would experience it at the same point in the movement each time a task was performed. Furthermore it was also hypothesized that the subject might begin to slow down at the point of pain and then be able to accelerate again after the pain diminishes. Subjects were instrumented using a Lumbar Motion Monitor (an exoskeleton attached to the back that can measure range of motion, velocity and acceleration in all three planes of motion). Several movement tasks requiring forward flexing and then extension and finally returning to the starting position were devised. This cycle was divided into 360-degrees so that each trial could be time-normalized to other trials on a position by-position basis. Using the LMM, it was established that movement information could be captured and stored including peak acceleration, average acceleration, peak velocity, average velocity as well as consistency. Other variables such as height, weight, length of limbs, position of foot, anthropometrical details, and other biomechanical factors of each individual were added to the collected data.

Two groups of subjects were tested. One was a group of 19 patients with chronic back pain. This fact was established both by history and by a physical performed by a physician. The second group of 20 had no history of back pain. Both groups were asked to perform the predetermined movement protocol tasks as best they could with full effort. Each group was then asked to repeat the same movement tasks, this time "pretending" they had back pain at a specific location in an attempt to convince us that they had real pain at that location. The goal was to find a group of variables that are readily measureable and, taken together, can reliably place an unknown individual into the correct group.

Over 100 movement and static variables for each subject were derived from the measurements. A statistical regression analysis, consistent with the teachings herein, was performed to see if any subset of these parameters, in combination, had enough predictive power to result in clustering of data that reliably placed a subject into the correct group (faking or non-faking). The analysis produced a formula with a 91 percent chance of placing an unknown individual into the proper group. The most salient factors were related to abruptness of change in acceleration near the point of pain and the consistency of that measure. The "fakers" did not produce the acceleration/deceleration profile at the point of "pain" to a degree and with consistency as to location and as to timing when compared to those with actual back disorders.

An executable protocol was developed to particularly instrument, compute, and evaluate the acceleration/deceleration profile at the point of inflection. This protocol could quickly and reliably categorize sincere and insincere self-reporting of back pain.

Example 3

Golf Performance Index

A sport performance example consistent with the principles taught herein is a "Golf Performance Index". GPI score is a scalar rating of overall level of performance in a golf skill. One way to think about this is as a process for transforming data comprising a time-series of values representing human motions into an objective meaningful measure providing that person's golf swing rating. While learning a new swing a subject may be progressing steadily in their mastery of that new skill but in fact be producing erratic end-results. To coach or to self-coach, an objective measure of progress in learning that swing other than by ultimate outcomes can be valuable. Determining an overall figure of merit of a swing execution based on minimal measurements (for cost reasons and to reduce the intrusive instrumentation borne by the golfer) is desired. A figure of merit or rating achievement of a desired swing can give more valuable feedback to a student than the final outcome of ball flight or golf score. These final outcomes are unduly affected by very small differences in execution or in external factors. Initially a comprehensive set of parameters that may contribute to the accuracy of a golf swing's result is postulated. Motion information is collected over a set of golfers representing a wide range of abilities. Also ball flight accuracy is measured. Those skilled in the art will understand that this can be accomplished either by golfers actually hitting balls or by a virtual golf simulation.

Correlations are determined between each motion parameter, combinations of motion parameters, and ball flight. This can be accomplished by classical linear regression techniques or by data mining techniques including clustering. As in other examples, this mathematical analysis can rank the various motions and measurements of the comprehensive set by their respective statistical predictive power. Keeping practicality of measurement in mind, a subset of motion parameters with effective predictive power is listed and forms the framework of an executable protocol. The number of parameters from the initial set that end up in the executable protocol is based on a desired degree of statistical confidence.

Example 4

Occupational Assessment

Rather than describe this example in detail, below is presented a problem amenable to attack by the methods taught herein.

An objective measurement of the capability of making particular job-related movements, particularly under load, is valuable in assessing workers. Periodically, employees can be tested as part of a program to promote safety and health as well as to assess the job-readiness of employees recovering from injury. In cases of recovering from disability, for example, an employee may be deemed ready to return to work when they have regained their pre-injury level in the relevant physical capability. Being able to objectively measure the employees in a job category and then know what level a particular person should be restored to before returning to work would save money and time.

Example Method of Creating Protocols

A method for developing an executable protocol includes the steps:

1) Accepting a specific domain of interest.
2) Selecting a comprehensive set of real-time motion-related parameters relevant to the domain of interest and selecting other variables to be measured or surveyed.
3) Accepting and storing data from multiple runs of performance with various subjects while those subjects perform the comprehensive set of movements while the comprehensive set of parameters are collected.
4) Analyzing resulting data by at least one of the following techniques: (a) non-linear data mining techniques to find classification clusters, decision tree classifiers, or ordinal, or scalar, or vector rating; and (b) classical statistical methods to determine correlations and other statistically valid relationships to allow meaningful classification or scalar or ordinal indices to be discovered.
5) Ranking the movements and the parameters of those movements by their statistical predictive power.
6) Selecting a subset of the comprehensive movements based on their ranking to comprise the movements and parameters of an executable protocol having a desired level of statistical reliability in classification or rating.

Protocol Method

Example method for administering a protocol by the steps of:
1) Instrumenting subject for predetermined, real-time motion-related measurements.
2) Performing, by a subject, a predetermined motion sequence. Collecting data regarding a predetermined set of parameters;
3) At least a subset of the collected motion information is formatted for computerized statistical analysis to produce a result that is (1) a classification or (2) an ordinal or (3) scalar rating.
4) Optionally permit real-time viewing of protocol performance by a remotely located monitor.
5) Optionally store video documenting protocol performance along with the data for later verification of correct protocol administration.

The data analyzing step can be performed at a different location and time than the actual testing of the subject.

Comprehensive Parameters

Those with subject matter knowledge in the application domain of interest may advantageously postulate an initial comprehensive set of factors. Preferably motions, measurements, and derived parameters to be "in the mix" of initial widely constituted measures can include: higher order quantities such as velocity and acceleration, consistency of performance in repeated motions, and angle/angle comparisons of pairs of coordinating body structures. Both motions constituting open kinetic chains and those constituting closed kinetic chains and those unloaded and loaded are also preferably in the initial comprehensive set of parameters. Spectrally pre-processed data, in addition to time-domain data may bring correlative relationships to light. In some cases it is preferred to also include body type, demographic, and psychological variables.

Programmed Computer Systems

For analyzing of measured and calculated parameters, data mining workbench software such as Weka, Orange, Matlab, IBM DB2 Intelligent Miner and statistical software tools such as SPSS can be used.

During Protocol Creation

Example method steps performed on data recording computer systems:
1) Filtering and normalize data.
2) Computing predetermined parameters from raw data (velocity determined from acceleration or kinetic information from kinematic information, for example).
3) Packaging data for use by an analysis system.

Data Analysis Computational Techniques—Protocol Development

One goal of some embodiments consistent with the teachings herein is to discern a subset of motions and subset of possible data measures of those motions to be automatically or semi-automatically analyzed during protocol execution. These subsets would be selected to include data of effective power to provide a protocol that achieves a desired trade-off in ease of administration and the statistical validity of result.

Traditional statistical techniques useful in the data analysis steps include regression, multivariate analysis, and principle component analysis (PCA). Those skilled in the art will be familiar with these mathematical approaches. They are shown applied in this art in U.S. Pat. No. 6,056,671, Manner; and Quantitative assessment of the control capability of the trunk muscles during oscillatory bending motion under a new experimental protocol, Kim, Parnianpour and Marras, Clinical Biomechanics vol. 11, no. 7, 385-391, 1996. Both references are hereby incorporated herein by reference in their entireties.

In many cases, the powerful, non-linear techniques of data mining including training artificial neural nets (ANN), self-organizing maps (SOM), machine learning classifier trees, and fuzzy decision trees are comprised in the data analysis. Those skilled in the art will be familiar with these computational approaches. They are shown applied in this art in US Published Patent Application 2005/0234309, Klapper, in U.S. Pat. No. 5,413,116, Radke et. al., and in U.S. Pat. No. 6,248,063, Barnhill. All three of these references are hereby incorporated herein by reference in their entireties.

Figure 3:
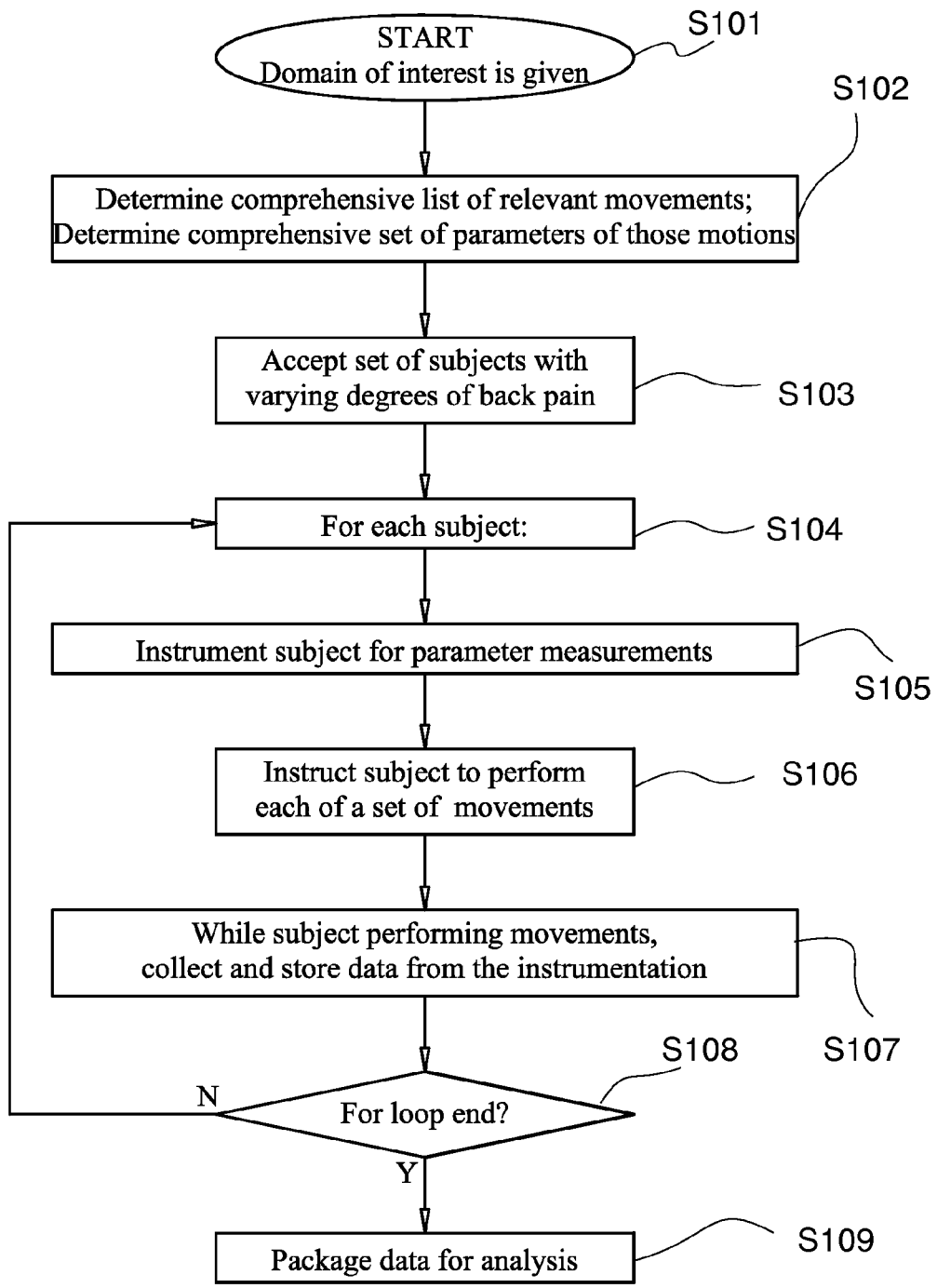
FIG. 3 is a flow chart of the data collection steps involved with an example embodiment of protocol creation.
Figure 4:
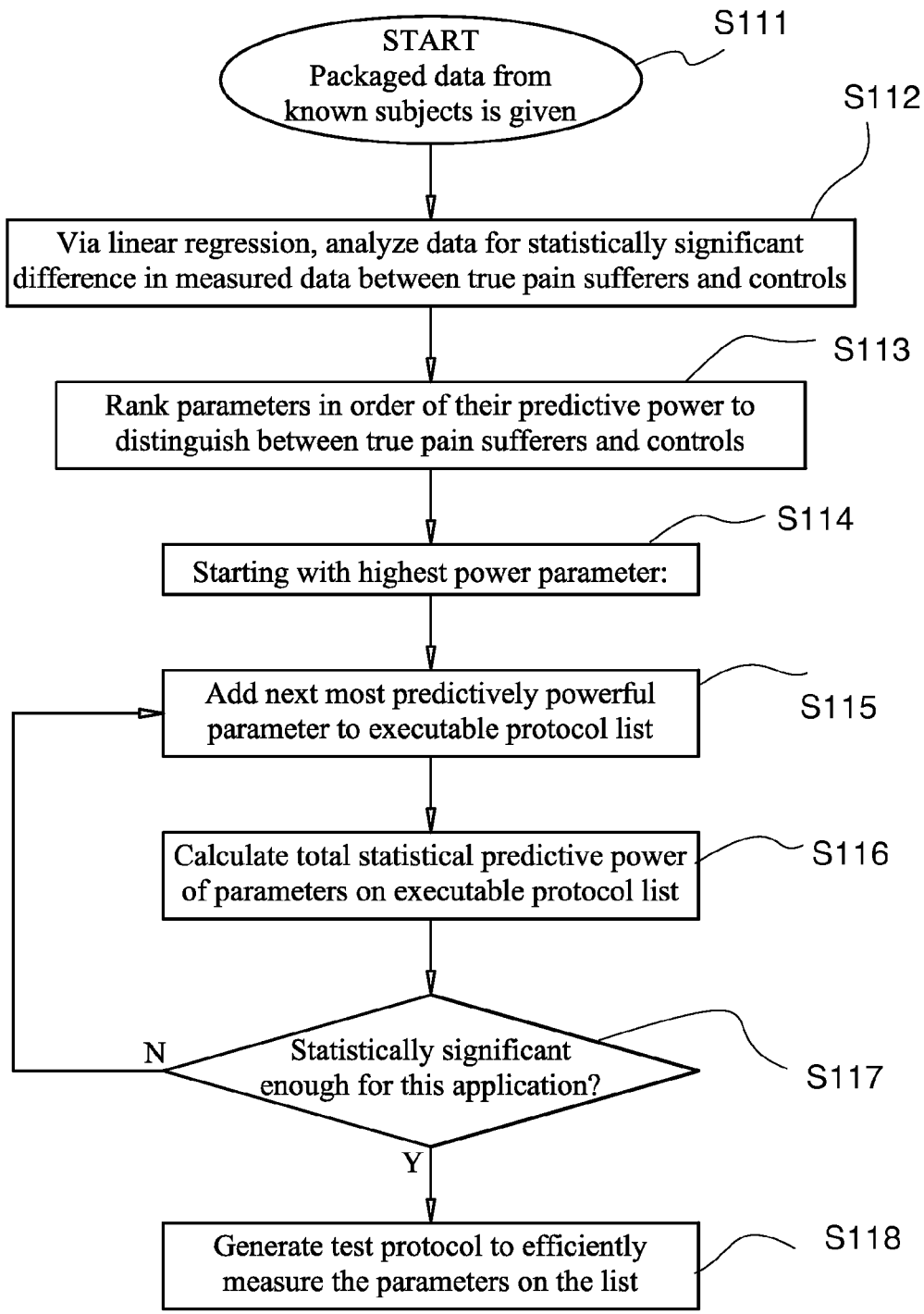
FIG. 4 is a flow chart of the data mining and analysis steps involved with an example embodiment of protocol creation.

In many implementations consistent with these teachings the initial data is from a large number of subjects with known attributes relative to the physical domain of interest. In other cases, for example with the use of "unsupervised" ANN or clustering techniques, there may not be subjects of known, quantified capabilities. For some protocol creations it may be advisable to have subjects of a known condition as well as "normals". In other cases one might have a subject population that is selected from subjects all suffering from a common condition but in varying degrees. In protocols for tracking changes in an individual, they are analyzed in light of their own performance at various stages of recovery, deterioration, learning, or circumstances. FIGS. 3 and 4 show flow charts of steps for creating an executable protocol.

FIGS. 3 and 4 together illustrate one example process for producing a protocol for distinguishing between individuals with back pain and individuals feigning back pain. The first step is determining or receiving a physical motion domain of interest S101. In this case back pain self-reporting veracity is the subject. In the next step a wide range of motions and measurements of those motions is postulated S102 as relevant to making the desired distinction. In the case of back pain, the rate and extent of spine movement is thought to be highly relevant. A Lumbar Motion Monitor that can measure position, velocity, and acceleration of the spine is selected to provide the raw data. The Lumbar Motion Monitor measures in the sagittal, lateral, and twisting planes. A set of subjects with an appropriately wide range of back problems is recruited and selected S103.

In creating the protocol, each subject selected goes through the same set of steps. In FIG. 3 this is expressed by initiating a FOR loop S104. The next steps involve instrumenting the subject at hand S105 according to the previously determined instrumentation and directing the subject to perform the previously determined motions S106. While the subject is performing, those movements', raw data associated with those movements is collected from the instrumentation and stored in a computer readable media S107. The end of the FOR loop for that subject is reached and if there are untested subjects S108 it is decided to return control to the top of that loop S104.

When it is determined that the last subject has been tested S108 the collected and stored data is packaged for analysis S109. This packaging might involve adding non-motion information, providing a copy of the data, or an address within a computer readable media to locate it. More frequently it will involve preprocessing the information to filter out noise and non-meaningful data. It also might involve norming, using principal component analysis for simplification of further data manipulation.

The sequence continues, as shown in FIG. 4 by taking the packaged data as a starting point S111. In this case the next step is to analyze the data using linear regression for variables in the packaged data having high correlation to the pre-known state of the individuals S112. In other, protocols consistent with these teachings, many other forms of analysis can be used. Data mining techniques like cluster analysis as well as artificial intelligence techniques including artificial neural networks might be used in this step.

In the case of a traditional statistical method such as linear regression, the various measured parameters will each have a correlation coefficient or other statistical confidence measure. The next step ranks the various parameters by that statistical quantity S113 with the most predictive first. In a version using cluster analysis, the parameter list might include a list of various subsets of the total, each subset in order by its power. Starting with the first parameter S114 the program module loops through the parameters from top down adding them S115 to the list being compiled of candidate measurement for the protocol being created. As each new parameter is added to the candidate list, the predictive power of the items on the list, taken together, is tested against the received packaged data S116. In FIG. 4 it is seen that this loop is ended when the candidate parameter list reaches a level that is deemed of a high enough significance S117 for the purposes of the protocol being created. In fact many processes consistent with the teachings herein will also assign a rating representing the practicality of making each type of measurement. This can allow optimization for foolproof-ness to administer or time to administer, for example. Therefore the cutoff as to significant-enough S117 could be set conservatively in order to allow for some "candidate" parameters to be rejected for use in the finally produced protocol due to protocol considerations.

After the list of parameters is established, a detailed plan to make those measurements efficiently using cost-effective instrumentation is created S118 which constitutes the basis of a protocol for; in this case, assessing the presence of back pain regardless of a subject's self-reporting.

During Protocol Execution

Example Data Collection Steps

Figure 5:
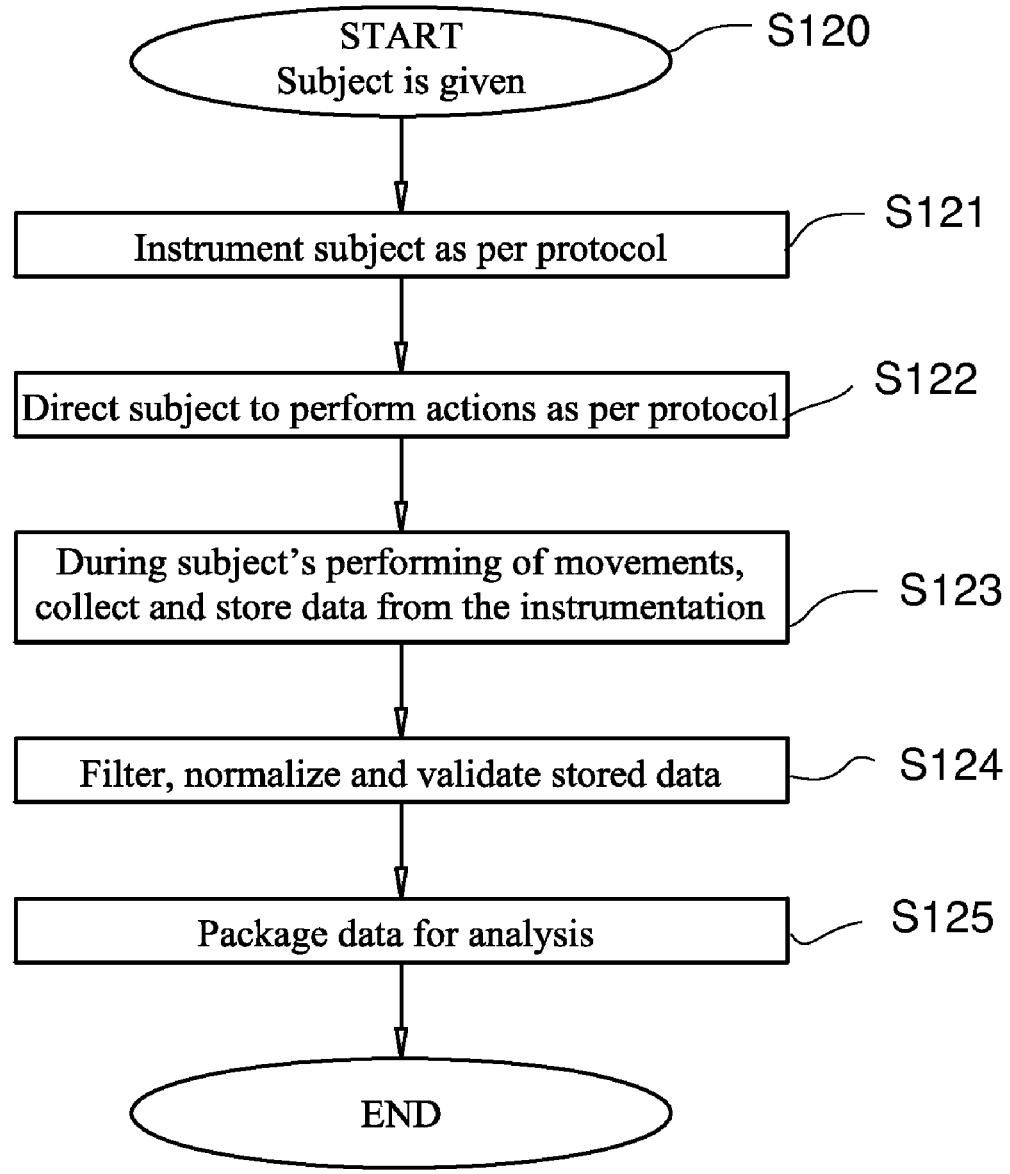
FIG. 5 is a flow chart of the data collection steps involved with an example of protocol execution.
Figure 7:
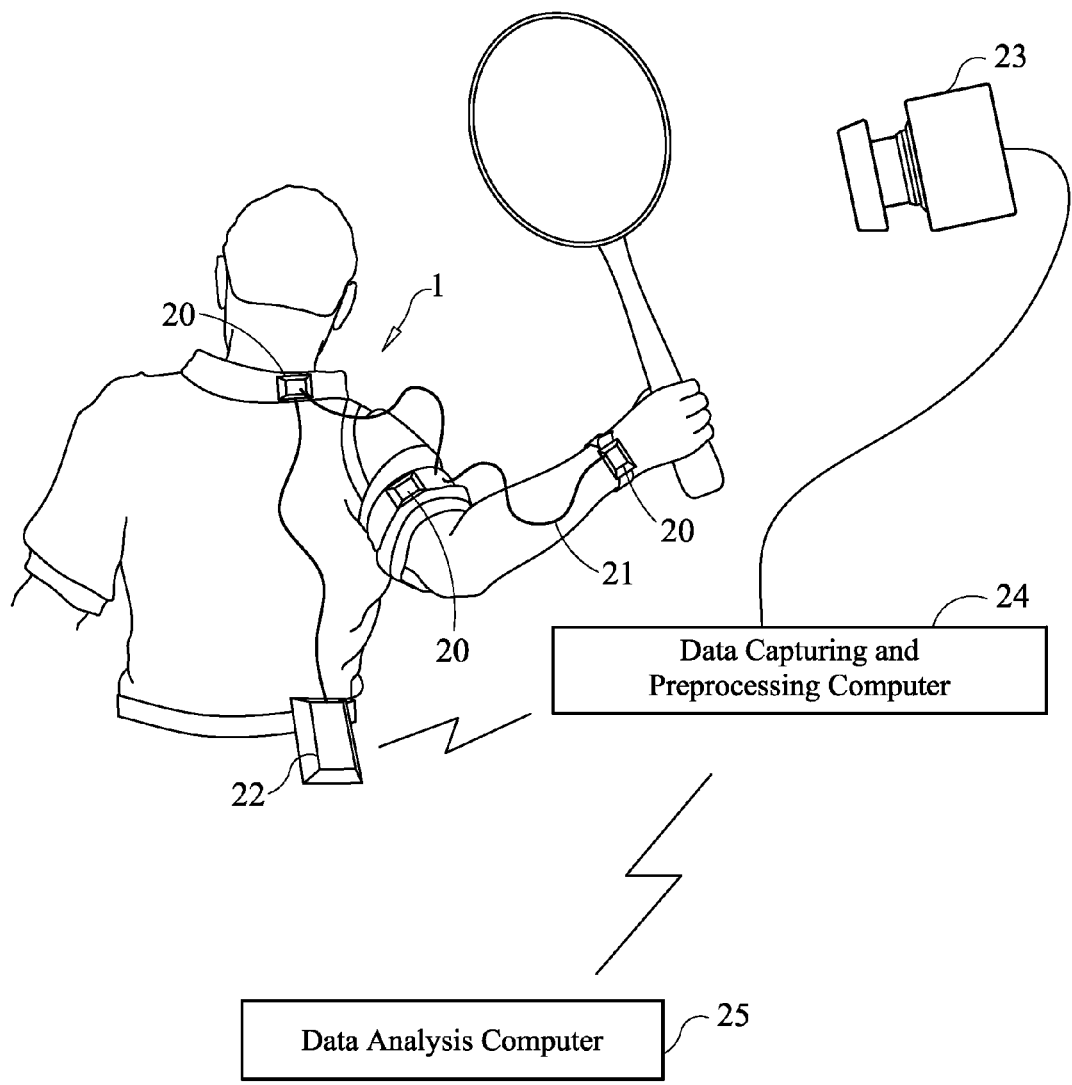
FIG. 7 illustrates a system for performing a protocol for evaluating a tennis swing; shown are a human subject with attached accelerometers at selected locations, a data capturing and preprocessing computer, and a data analysis computer.

FIG. 5 shows a flowchart of the data collection steps of an example executable protocol. Instrumentation that might be used in a tennis application is illustrated in FIG. 7 and further discussed herein.

Example Data Analysis Steps Performed by a Data Analysis Computer System
1) Accepting movement and force information from pre-processing system.
2) Doing at least one of: (a) applying predetermined decision tree (b) feeding data to trained machine learning data structure to determine classification or rating (c) applying linear or non-linear model.
3) Based on step 2 determine closet match under predetermined rules and set as a rating.
4) Outputting rating.

Figure 6:
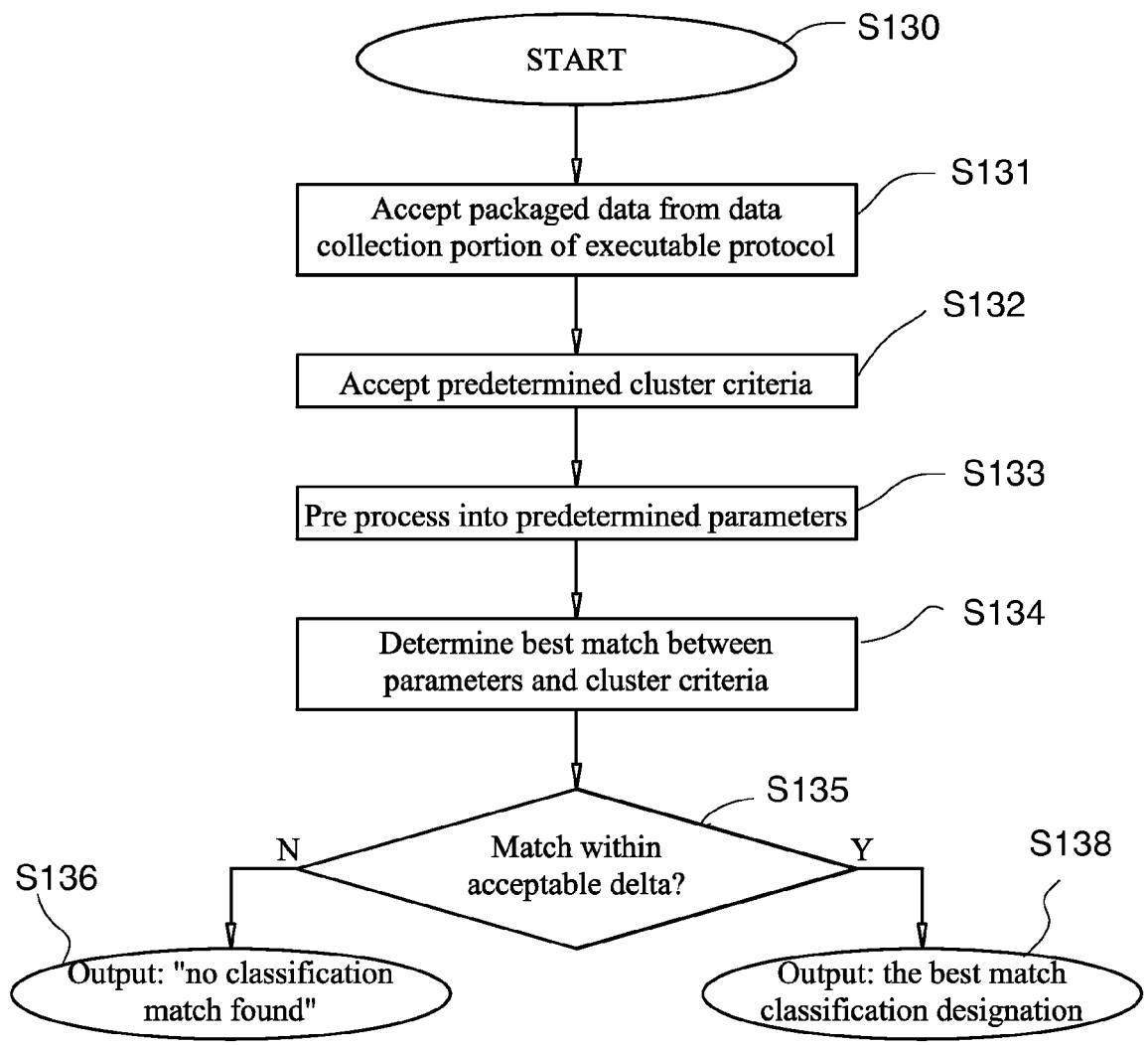
FIG. 6 is a flow chart of the data mining and analysis steps involved with an example embodiment of protocol creation.

A flow chart illustrating an example of the steps involved in data analysis during protocol execution is seen in FIG. 6.

Data Analysis Computational Techniques—for Protocol Execution

The data produced while testing an unknown subject may be first pre-processed to extract pre-determined features. The data may be normalized in one or more dimensions. A rating or categorization may be assigned by linear calculation, by following a classification tree, or by providing data to a trained learning machine.

FIGS. 5 and 6 represent flowcharts of executing a pre-defined protocol for assigning an "unknown" subject to one of multiple pre-identified clusters. FIG. 5 covers activities directly related to testing the individual while FIG. 6 relates to steps taken to analyze the information from the tests.

The first step of FIG. 5 is receiving S120 the given subject. The next step is to instrument that subject S121 for motion measurements as dictated by the specific protocol being performed (back pain, tennis swing, gait, etc). A prescribed series of motions is performed S122 by the subject while the motion data is being electronically recorded S123 on suitable machine-readable media. Preprocessing steps that might be performed at the time and place of the test include filtering, normalizing, and extracting biomechanical information S124 from the recorded raw data transforming it into a reduced and more meaningful state. Presuming that the analysis is done separately from the information collection, the information is then suitably packaged S125 for analysis. As shown, the analysis is optionally performed at a different location on a different computer system.

The information transformation and analysis of that data is shown in FIG. 6. After the data is accepted S131, the clustering criteria to be applied to that data is accepted S132. In this example, the accepted, preprocessed data is further processed S133 to extract salient features specified by the clustering criteria to use as inputs for cluster match determination S134. That cluster-matching step involves a computer-implemented, mathematical comparison of the salient features of the accepted data to pre-defined, denoted, clusters of parameters specified in the accepted cluster criteria.

If the transformed information representing the subject's motions is found to conform to a denoted cluster with a predetermined degree of statistical acceptability S135, the denotation of that match is output S138. In the case that the measured motion data of the subject does not align with any predetermined cluster to an effective degree, the output is that no classification is clearly indicated S136 by the data.

System

An example system for executing a protocol consistent with the principles taught herein is shown in FIG. 7. A person 1 is instrumented in a minimal fashion with accelerometers 20 in three chosen locations. The accelerometers are coupled via cables 21 to a belt-mounted controller 22. The controller communicates by Bluetooth compliant wireless signals with a local data capturing and pre-processing computer 24 for recording, initial filtering, normalization and formatting. In one respect, the data capturing and pre-processing computer follows instruction to act as an intelligent electronic recorder. In turn that system communicates with a remotely located analysis and rating system 25. An alternate example system can comprise, as its hardware portion, a home console gaming system such as a Wii with motion and force sensor inputs. Portions of a system can comprise one or more devices like an iTouch or iPhone, which can have accelerometers, GPS, and computational capabilities.

System Variations

Other system versions might instrument the human with an upper body, lower body or full body suit such as suits in the MVN brand product line offered by Xsens Technologies B.V. and illustrated in FIG. 2A. For some applications the motion or force sensors of a home game system's input device or those in a portable device such as an iTouch may be adequate to make the measurements.

The data preparation system and data analysis and rating system might be remote, might be co-located, or might be implemented on a single computer server. The computational devices used to carry out the method could be a personal computer. In some versions, the system might prompt the subject to perform the limited set of motions. This might be via a text display, by spoken output, or preferably by a video demonstration. In addition, a particular system version could provide a warning that a sequence of motions was not performed as per-protocol and inform the subject or clinician. In some cases, the subject and the computer performing the analysis might not be co-located. At a central facility for data analysis computation, trained computer learning systems, and expertise may serve many protocol execution sites. A camera 23 might be used to capture still or video images of the protocol execution to be stored along with the motion data for future verification of correct protocol administration.

Some embodiments will be broken down into foolproof steps, figuratively a "paint-by-numbers" execution protocol. At another time and location more trained personnel can carry out other steps of data analyzing and assignment of discrete classification or of a rating. Below is a pseudo code "flowchart" of an example protocol execution for rating a tennis swing.

Pseudo Code of Protocol Execution

```
START
  Instrument Subject, in a predetermined manner for position, motion and
  force sensing;
  Operatively couple sensing equipment to data capture computer;
  Initiate information capturing by sensors and data capture computer;
  Direct subject to perform predetermined tennis swing motion sequences
  while capturing motion and force and position information;
  Capture photographic information of subject while subject is performing
  predetermined motion sequences;
  Command data analysis computer to pre-process captured information and
  format and package for analysis;
  Operatively communicate formatted and packaged information from data
  capture computer to data analysis computer;
  Command data analysis computer to statistically compare information
  communicated from data capture computer to a database of a set of
  predetermined quantitative criteria of movement performance;
  Is there statistically significant agreement of packaged information and
  predetermined criteria?
      TRUE: Output numerical rating associated with criteria match
      FALSE: Output: "No reliable match found"
  END
```

The various illustrative program modules and steps described in connection with the embodiments disclosed herein may be implemented as electronic hardware, computer software, or combinations of both. The various illustrative program modules and steps have been described generally in terms of their functionality. Whether the functionality is implemented as hardware or software depends in part upon the hardware constraints imposed on the system. Hardware and software may be interchangeable depending on such constraints. As examples, the various illustrative program modules and steps described in connection with the embodiments disclosed herein may be implemented or performed with an application specific integrated circuit (ASIC), a field programmable gate array (FPGA) or other programmable logic device, discrete gate or transistor logic, discrete hardware components, a conventional programmable software module and a processor, or any combination thereof designed to perform the functions described herein. The processor may be a microprocessor, CPU, controller, microcontroller, programmable logic device, array of logic elements, or state machine. The software module may reside in RAM memory, flash memory, ROM memory, EPROM memory, EEPROM memory, hard disk, a removable disk, a CD, DVD or any other form of storage medium known in the art. An example processor may be coupled to the storage medium so as to read information from, and write information to, the storage medium. In the alternative, the storage medium may be integral to the processor.

In further embodiments, those skilled in the art will appreciate that the foregoing methods can be implemented by the execution of a program embodied on a computer readable medium either tangible or intangible. The medium may comprise, for example, RAM accessible by, or residing within the device. Whether contained in RAM, a diskette, or other secondary storage media, the program modules may be stored on a variety of machine-readable data storage media such as a conventional "hard drive", magnetic tape, electronic read-only memory (e.g., ROM or EEPROM), flash memory, an optical storage device (e.g., CD, DVD, digital optical tape), or other suitable data storage media.

Those skilled in the art will recognize that the embodiments described herein are readily producible using known techniques, materials and equipment. This teaching is presented for purposes of illustration and description but is not intended to be exhaustive or limiting to the forms disclosed. Many modifications and variations will be apparent to those of ordinary skill in the art. The claims below, in contrast, set out its metes and bounds. In the claims, the words "a" and "an" are to be taken to mean "at least one" even if some claim wording explicitly calls for "at least one" or "one or more". In addition any predetermined value, criteria, or rule in the claims may be predetermined at any time up to the time it is required for effective operation unless explicitly stated otherwise.

What is claimed:

1. A method of producing a protocol comprising:
    (a) accepting a time-series of values representative of parameters of a plurality of body locations on a plurality of individuals while those individuals perform a plurality of motion tasks;
    (b) analyzing those values with a data mining computer program running on a computer system to effectively assign at least a portion of the plurality of individuals into one of at least two groups based upon that analyzing of the time-series values, each group being composed of individuals having a common physical attribute;
    (c) identifying one or more subsets of the parameters, and of the associated body locations, and of the associated motion tasks, respectively, that collectively possess effective statistical power to assign an individual to their proper group; further;
(d) identifying rules, that when applied to the subset of the parameters, and of the associated body locations, and of the associated motion tasks properly assigns an individual to their proper group;
(e) enumerating the subsets and rules for application to an unknown subject for effectively assigning the unknown subject to their proper group.

2. The method of claim 1 further comprising the step of measuring a time-series of values related to the position of a plurality of body regions on at least one individual.

3. The method of claim 1 where the physical capability is related to a sport skill.

4. The method of claim 2 where the physical capability is related to a medical condition.

5. The method of claim 2 wherein the step of measuring comprises tracking a plurality of body positions by three-dimensional image video recording.

6. The method of claim 2 wherein the step of measuring comprises measurements representative of joint angles.

7. The method of claim 1 wherein the at least two groups comprise a group of individuals with back pain and a group of individuals feigning back pain.

8. The method of claim 1 further comprising:
(i.) accepting a time-series of values representative of at least a portion of the enumerated parameters taken from a subject performing at least a portion of the enumerated motion tasks;
(j.) analyzing the accepted values according to at least a portion of the enumerated rules;
(k.) assigning the subject to a group based upon the analyzing of that subjects' accepted values.

9. A method of producing a protocol for assessing a given aspect of a human's physical performance comprising the steps of:
a. measuring, and recording in non-transient computer readable memory, human movement parameters from a series of performed movements for a set of human subjects, each subject respectively having a known capability in the given aspect of physical performance;
b. data mining, using an electronic computer executing a data mining application program, to identify correlations between the subjects' recorded movement parameters and their respective known capability in the given domain;
c. identifying a sensitive subset of the movement parameters, such that the sensitive subset collectively has adequate statistical correlative power to predict the known capabilities at a predetermined confidence level;
d. determining, from the data mining results, criteria for ascribing one or more distinct capability designations in the given aspect of physical performance to an unknown subject based upon that unknown subject's performance on the identified subset of movements;
e. enumerating the identified subset of movements and their respective parameters, and enumerating the determined criteria and their respective designations of degree of physical performance, thereby producing an assessment protocol.

10. The method of claim 9 wherein the given aspect of physical performance relates to a game.

11. The method of claim 9 in which said data mining comprises a non-linear data clustering technique.

12. The method of claim 9 in which said data mining comprises a linear statistical hypothesis testing technique.

13. The method of claim 9 in which said data mining comprises an artificial neural net technique.

14. The method of claim 9 further comprising: determining relevant human movement parameters to be measured and the associated specific movements to be performed while measuring, for a given aspect of human physical performance.

15. The method of claim 9 wherein the at least one of the one or more distinct capability designations is an ordinal value.

16. The method of claim 9 wherein at least one of the one or more distinct capability designations is a scalar value.

17. The method of claim 9 wherein measuring and recording parameters comprise real-time position measurements of at least two predetermined body locations.

18. A method of rating a given physical capability of a human, comprising:
ascribing a rating to a given motion-related physical capability of a subject by analyzing a time-series of information representing the relative motion between at least two predetermined points, each respectively related to the subject's body position, while that subject performs a predetermined motion task;
wherein a point related to the subject's body position is either a specific location on the body, or optionally, a location on an article in contact with the body;
further, the ascribed rating is determined by detecting a similarity between the time-series of information and time-series information from corresponding measurements made on one or more individuals performing the predetermined motion task; the similarity criteria for ascribing a rating being based upon predetermined rules.

19. The method of claim 18 further comprising the steps of measuring and storing real-time data from which the time-series of information representing the relative motion between at least two points while that subject performs a predetermined motion task is derived.

20. The method of claim 19 wherein the measuring and storing are performed at a distinct geographic location from that where at least one of the analyzing, detecting and ascribing steps are preformed.

21. The method of claim 18 wherein at least one predetermined rule comprises at least one factor of substantial weight that is representative of rate of acceleration.

22. The method of claim 18 wherein at least one predetermined rule comprises at least one factor of substantial predetermined weight that is representative of comparison of a dynamic angular relationship of one body portion to another body portion.

23. The method of claim 18 wherein the predetermined motion tasks do not substantially consist of a sequence of motions normally performed in demonstrating the given physical capability.

24. The method of claim 18 wherein at least one rating signifies a high probability of back pain and another rating signifies a high probability of feigning back pain.

25. A protocol for assessing a degree of human capability in a given physical activity domain comprising the steps of:
a. instrumenting the human to allow measuring a predetermined set of movement parameters;
b. performing, by the instrumented human, a predetermined set of movements;
c. measuring and storing on a computer readable media, movement information derived from the instrumenting during the performing;
d. pre-processing the stored information into a form suitable for comparing;

e. comparing pre-processed information to predetermined criteria;

the predetermined criteria previously derived from tests conducted on a variety of humans with known capabilities in the domain;

f. assigning to the human, a designation of capability in the physical activity domain based on the results of the comparing to predetermined criteria.

26. The protocol of claim 25 wherein the designation of capability represents an overall figure of merit of the capability of the subject in the given domain.

27. The protocol of claim 25 wherein the steps of instrumenting and performing occur at a location distinct from that of the steps of comparing and assigning.

28. The protocol of claim 25 wherein the instrumenting comprises placing accelerometers in proximity to the subject's body.

29. The protocol of claim 25 wherein the instrumenting comprises configuring video imaging to track portions of the subject's body.

30. The protocol of claim 29 wherein portions of the subject's body are marked to facilitate their identification and tracking by video imaging.

31. A method of associating a discrete designation to a given physical capability of a subject, comprising:

a) a step for accepting data that effectively characterize the movement of two or more of a subject's body portions in relation to each other, while the subject performs a series of motions indicated by predetermined rules;

b) a step for assessing a degree of similarity of the subject's characterized movement with respect to comparable characterizations of comparable movements made by a plurality of individuals; the individuals each having respective designations in the given physical capability;

c) a step for associating a discrete designation to a given physical capability of a subject based upon said step for assessing.

32. The method of claim 31 wherein said step for accepting data comprises recording a force measurement between the body and an object.

33. The method of claim 31 wherein said step for accepting data comprises recording electrical activity readings of at least two related muscles.

34. The method of claim 31 wherein said step for acquiring data comprises position tracking of at least two body portions.

35. A system for transforming human motion data into an objective rating comprising:

a. at least one of: one or more motion sensors, one or more angle sensors, and one or more pressure sensors for instrumenting a human performing one or more motions;

b. a first computer communicatively coupled to said sensors, said computer adapted to receive data representative of motion from said sensors; the first computer is programmed to capture, store and pre-process the data received from sensors;

c. a second computer communicatively couplable to said first computer; said second computer programmed for analyzing the pre-processed motion data in light of a plurality of pre-collected data motion from known subjects, said analysis to produce a discrete result indicative of a level of performance.

36. The system of claim 35 such that said second computer is operationally locatable other than proximate to the location of the subject's performance.

37. The system of claim 35 wherein said first computer further comprises programming to store video images of the human performing the one or more motions; and said second computer accepts and stores image information regarding the performance of the one or more motions.

38. A non-transient computer-readable medium containing instructions executable by a computer, said instructions directing the steps of:

a) accepting movement and force information representative of a human performing a series of movement tasks;

b) processing the movement and force information to extract biomechanical information;

c) comparing the biomechanical information for an effective match with data representative of biomechanical information related to a plurality of comparable movement tasks performed by a plurality of subjects, the subjects each respectively, having a known rating of a common physical capability;

d) assigning a designation of capability to the human according to detecting an effective match between the human's biomechanical information and that of one or more of the subjects, an effective match being determined by predetermined criteria.

39. The non-transient computer-readable medium of claim 38 wherein the instructions executable on a computer further comprise: the comparing step includes effective match criteria based on cluster analysis.

* * * * *

UNITED STATES PATENT AND TRADEMARK OFFICE
CERTIFICATE OF CORRECTION

PATENT NO. : 8,139,822 B2  
APPLICATION NO. : 12/792088  
DATED : March 20, 2012  
INVENTOR(S) : Allen Joseph Selner Page 1 of 1

It is certified that error appears in the above-identified patent and that said Letters Patent is hereby corrected as shown below:

In the Claims

Column 14, claim 20, line 41, "preformed" should be changed to --performed--.

Signed and Sealed this  
Eighth Day of July, 2014

Michelle K. Lee  
*Deputy Director of the United States Patent and Trademark Office*